United States Patent [19]

Ashley-Rollman et al.

[11] Patent Number: 4,943,770
[45] Date of Patent: Jul. 24, 1990

[54] DEVICE FOR ACCURATELY DETECTING THE POSITION OF A FERROMAGNETIC MATERIAL INSIDE BIOLOGICAL TISSUE

[75] Inventors: Charles Ashley-Rollman; Miles C. O'Donnell, both of Andover; William McCormick, Carlisle, all of Mass.

[73] Assignee: McCormick Laboratories, Inc., North Chelmsford, Mass.

[21] Appl. No.: 328,443

[22] Filed: Mar. 24, 1989

Related U.S. Application Data

[63] Continuation of Ser. No. 40,614, Apr. 21, 1987, abandoned.

[51] Int. Cl.$^5$ .......................... G01B 7/14; G01V 3/10; A61B 5/06; G01N 27/72
[52] U.S. Cl. ................ 324/207.17; 128/737; 324/225; 324/233; 324/239
[58] Field of Search ................. 324/67, 133, 207, 233, 324/239–243, 329, 225; 361/180; 128/737; 340/551, 572

[56] References Cited

U.S. PATENT DOCUMENTS

| | | |
|---|---|---|
| 2,321,356 | 6/1943 | Berman . |
| 2,442,805 | 6/1948 | Gilson ............................ 128/737 X |
| 2,549,567 | 4/1951 | Berman . |
| 3,309,690 | 3/1967 | Moffitt ........................... 324/133 X |
| 3,371,272 | 2/1968 | Stanton . |
| 3,418,572 | 12/1968 | Humphreys, Jr. .................... 324/67 |
| 3,422,346 | 1/1969 | Hammer ............................ 324/233 |
| 3,436,649 | 4/1969 | Takechi et al. .................... 324/243 |
| 3,460,528 | 8/1969 | Carney ........................... 128/737 X |
| 3,528,402 | 9/1970 | Abramowitz . |
| 3,826,973 | 7/1974 | Pflaum ............................ 324/233 X |
| 3,847,157 | 11/1974 | Caillouette et al. ................ 128/348 |
| 4,063,561 | 12/1977 | McKenna ........................... 128/351 |
| 4,095,180 | 6/1978 | Brown ............................. 324/233 |
| 4,096,432 | 6/1978 | Spencer .......................... 324/233 X |
| 4,350,951 | 9/1982 | Jasper ............................ 324/133 |
| 4,416,289 | 11/1983 | Bresler ........................... 128/737 |
| 4,431,005 | 2/1984 | McCormick ........................ 128/737 X |
| 4,445,501 | 5/1984 | Bresler .......................... 128/737 X |
| 4,514,692 | 4/1985 | Johnson et al. ................... 324/233 X |
| 4,709,213 | 11/1987 | Podhrasky ........................ 324/233 X |

OTHER PUBLICATIONS

Cullen et al., "A New Method of Positioning Endotracheal Tubes", *Anesthesiology*, vol. 43, No. 5, Nov. 1975, pp. 596–599.

*Primary Examiner*—Gerard R. Strecker
*Attorney, Agent, or Firm*—Fish & Richardson

[57] ABSTRACT

A device for accurately detecting and monitoring the position of an object inside biological tissue, particularly an endotracheal tube inside a patient's throat, comprising a circuit which generates an electromagnetic field of limited width and depth, and which is disturbed by the presence of material having a high magnetic permeability such as a metal band on the distal end of such an endotracheal tube, but which is otherwise stable and not affected by temperature or other such factors. Included in the invention is a probe for generating the electromagnetic field, which probe is insensitive to temperature changes.

21 Claims, 4 Drawing Sheets

DEVICE FOR ACCURATELY DETECTING THE POSITION OF A FERROMAGNETIC MATERIAL INSIDE BIOLOGICAL TISSUE

This is a continuation of co-pending application ser. no. 040,614 filed on Apr. 21, 1987, now abandoned.

FIELD OF THE INVENTION

This invention relates to a device for accurately detecting the position of an object inside biological tissue, particularly a ferromagnetic material in the end of an endotracheal tube as it is positioned in the trachea or windpipe of a medical patient.

BACKGROUND OF THE INVENTION

It is necessary to insure that the breathing passageways of certain medical patients, e.g., those in surgery or intensive care, are kept oPen at all times. This is accomplished in the prior art by means of an endotracheal tube which is inserted through the patient's nose or mouth and extends through the patient's throat and into the patient's windpipe or trachea. These prior art tubes are hollow and open at both ends, and the end that extends outside the mouth or nose is anchored in place, usually with tape. Air can then pass through the tube into and out of the patient's lungs.

The principal drawback of the prior art tubes is that the distal end of the tube inside the patient must be inserted to and kept at a relatively specific position which is at about the midpoint of the trachea. This is because if the tube is inserted too far into the trachea, its distal end may extend into the bronchial tree for one lung, and thus the other lung will receive no air and collapse. On the other hand, if the distal end of the tube is not inserted far enough, it may interfere with the vocal cords. Another related problem is that as the tube is being inserted, the distal end may enter the esophagus, which is behind the trachea, and no air may reach the lungs.

In a normal adult the trachea is about 11 centimeters in length, and the distal end of the tube is generally properly positioned at the trachea's approximate midpoint. It may be anchored in place there by expanding a balloon attached to the tube. This positioning, however, has much less margin for error in children or infants, whose tracheas are much shorter in length. Furthermore, for both adults and children, even if the tube is properly positioned initially, movement of the patient often causes the tube to move up or down, and therefore the location of the distal end of the tube must not only be positioned properly to begin with, but it must also be continuously monitored.

The prior art used several methods for determining the position of a tube inside a patent. First, the tube position can be determined by x-ray, but notwithstanding the possible adverse effect of continued exposure to x-rays, the principal drawback of this method is that by the time the x-ray is taken, developed and returned, the tube may have moved again. Accordingly, the most common real time monitoring methods involve listening to the chest to hear if both lungs are filling and visually observing of the depth markings on the exposed tube. Neither of these methods, however, is very precise.

Two earlier patents, Bresler U.S. Pat. No. 4,416,289 and Bresler U.S. Pat. No. 4,445,501, both assigned to the same assignee as this application and both incorporated herein by reference, disclose devices for determining the position of an endotracheal tube inside a patient in real time. In both, a narrow electromagnetic field is generated, which is disturbed when a band of ferromagnetic material on the distal end of an endotracheal tube enters it. As the field penetrates tissue without effect, the band disrupts the field when the endotracheal tube is positioned in the patient's throat. Since the field is small and narrow, the band (and hence the distal end of the tube to which it is attached) can be accurately detected and monitored in real time. This is far superior to the prior art methods.

As significant an advance as these devices are, however, there are two additional areas in which operation could be improved. First, in addition to detection per se, there should be a specific and predictable correlation from instrument to instrument between the response or triggering of the device and the distance between the device and the metal band. Specifically, the device should not be triggered even if it is directly above the band when the band is beyond a certain very short distance from the device. The reason is to avoid detecting the tube if it is in the esophagus. As the esophagus is located behind the trachea for a supine patient, absent a specific (and limited) uniform depth of detection for the devices, a tube could be detected as being properly in place when in fact it is actually in the esophagus behind the trachea. As a result, it is desirable to have an instrument that will detect the tube in the trachea but not when it is in the esophagus immediately behind it. This should be true for each instrument and for each size tube (Pediatric or adult).

Secondly, it is important that the device be relatively insensitive to changes in temperature and other such conditions. In some situations, temperature changes may cause a physical expansion or contraction of the windings used to generate the field. If this causes the field to become unbalanced, a false detection signal may result. Because of this, it is not advisable to use these devices under certain conditions, such as emergency treatment outdoors, because of the possibility that a false detection signal due to temperature change could be interpreted as an actual detection signal.

Accordingly, a general object of the invention is to provide a device for aiding in initially positioning and later monitoring an endotracheal tube in a patient's trachea in real time.

A specific object of the invention is to provide such devices which uniformly have a limited depth of detection so as to avoid detection signals when there is esophageal intubation.

Another specific object of the invention is to provide such a device in which the field windings and overall circuit are not sensitive to temperature or other such changes that would otherwise unbalance the field or produce a circuit change that would result in a false detection signal.

SUMMARY OF THE INVENTION

We have discovered a device for accurately detecting and monitoring the position of an object inside biological tissue comprising a circuit which generates an electromagnetic field of limited width and depth, and which is disturbed by the presence of material having a high magnetic permeability, but which is otherwise stable and not affected by temperature or other such factors.

In the preferred embodiment, a probe having a primary winding and two main secondary windings is used to detect an endotracheal tube with a metal band near its distal end. The primary winding is excited by a 30 KHz oscillator, the output from which is supplied to the winding through a driver circuit which provides the large currents needed. The primary winding of the probe then creates an electromagnetic field encompassing the two series-connected secondary windings thereby inducing voltages in them. The respective voltages from the secondary windings cancel each other out as long as the field remains balanced. The band of metal at the distal end of an endotracheal tube disturbs the field. When the band comes near the axis of one of the secondary windings, that winding draws more flux resulting in a greater voltage induced across it. The voltages across the secondary windings no longer cancel, and this results in a net output voltage, which is used to produce a detection signal.

Any net voltage from the secondary windings of the probe is first amplified and then sent to a synchronous detector, which, as it is clocked by the original 30 KHz oscillator, rejects signals not originating with the probe windings. At the same time, the detector also converts the a.c. voltage to a d.c. signal essentially without error which provides temperature stability for the circuit. This d.c. signal, the magnitude of which is indicative of the proximity of the metal band, is then converted to a proportional frequency by means of a precision voltage-to-frequency converter. The converter has a well-defined threshold voltage which assures not only that the device has a specific predetermined sensitivity (set to exclude detection of a tube in the esophagus), but also that each device has the same sensitivity, and circuit variations due to temperature changes are further minimized. Any output frequency from the converter is then divided and used to drive the detection alarms, which include both an audio beeper and a light-emitting diode. In addition, the circuit includes a comparator, which is used to activate the light-emitting diode as an early visual indication of detection, and a voltage regulator which supplies a constant voltage to key elements of the circuit even if the battery voltage fluctuates or drops. A low battery voltage detector is also provided.

The temperature stability of the device as well as the specific limited field it generates also depends on the probe itself. The probe is comprised of a core of polycarbonate and glass fill which has a limited coefficient of thermal expansion. Grooves are machined into the core for the windings, and there are separate grooves for the primary winding and each of the two secondary ones. A fourth groove is also made for an adjustment winding, if needed, to help balance the two secondary windings. The windings themselves are uniformly layered and epoxied to the core. In addition, once the winding is complete, epoxy is applied by vacuum impregnation to the windings. Stabilization of the probe is enhanced by repeatedly baking and cooling the probe with its balanced windings. In addition to assure that any expansion of the secondary windings that does occur occurs uniformly to both (to keep the field balanced), an expansion groove is added to the core adjacent to the secondary winding farthest away from the probe's tip. The result is a probe that is not susceptible to giving false signals due to temperature changes or other similar factors and which can be reproduced so that any number of such probes will give the same response under the same circumstances.

DESCRIPTION OF THE PREFERRED EMBODIMENT

Drawings

We now turn to a description of the preferred embodiments, after first briefly describing the drawings.

STRUCTURE

Figure 1:
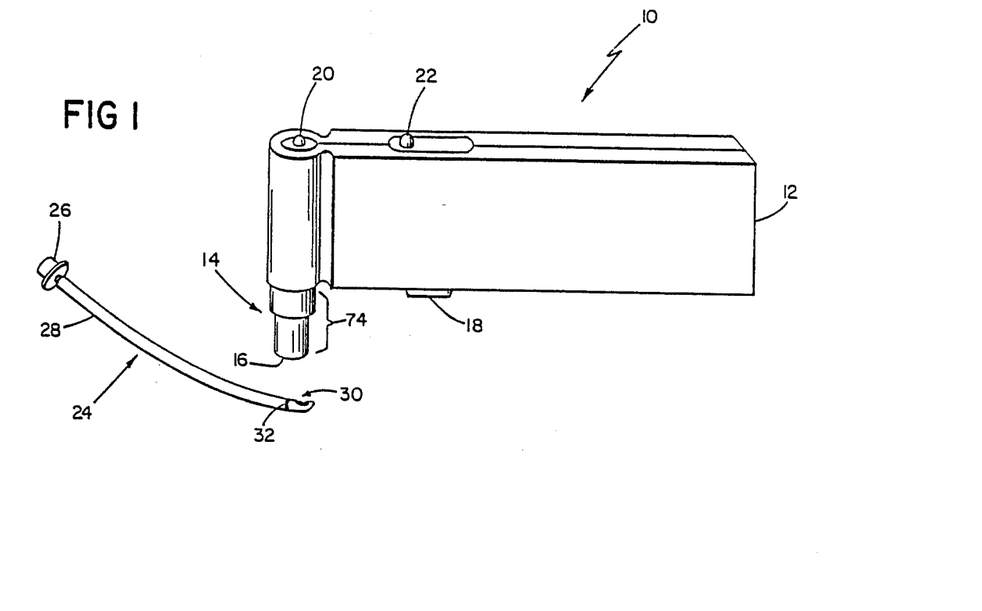
FIG. 1 is a perspective view of the device of this invention with an endotracheal tube having a metal band near its distal end.

Referring to FIG. 1, the detector of this invention is shown at 10. It generally comprises a circuit box 12 having a probe 14 with a detecting tip 16. A switch 18 is provided on the bottom of the box 12, and a (red) alarm light-emitting diode 20 is positioned near the probe 14 opposite its detecting tip 16. A second (green) light-emitting diode 22 is disposed on top of the box 12 as a battery level indicator. An endotracheal tube 24 for use with the detector 10 is also shown in FIG. 1. The tube 24 generally comprises a connector 26, which is disposed outside the patient's mouth when the tube is in place, and a hollow tube 28 extends from the connector to a distal tip 30. A metal band 32 is disposed near the distal tip 30. The specific tube 24 and the method of making it are disclosed in U.S. Pat. Application Ser. No. 810,015 filed Dec. 17, 1985 incorporated herein by reference.

Figure 3:
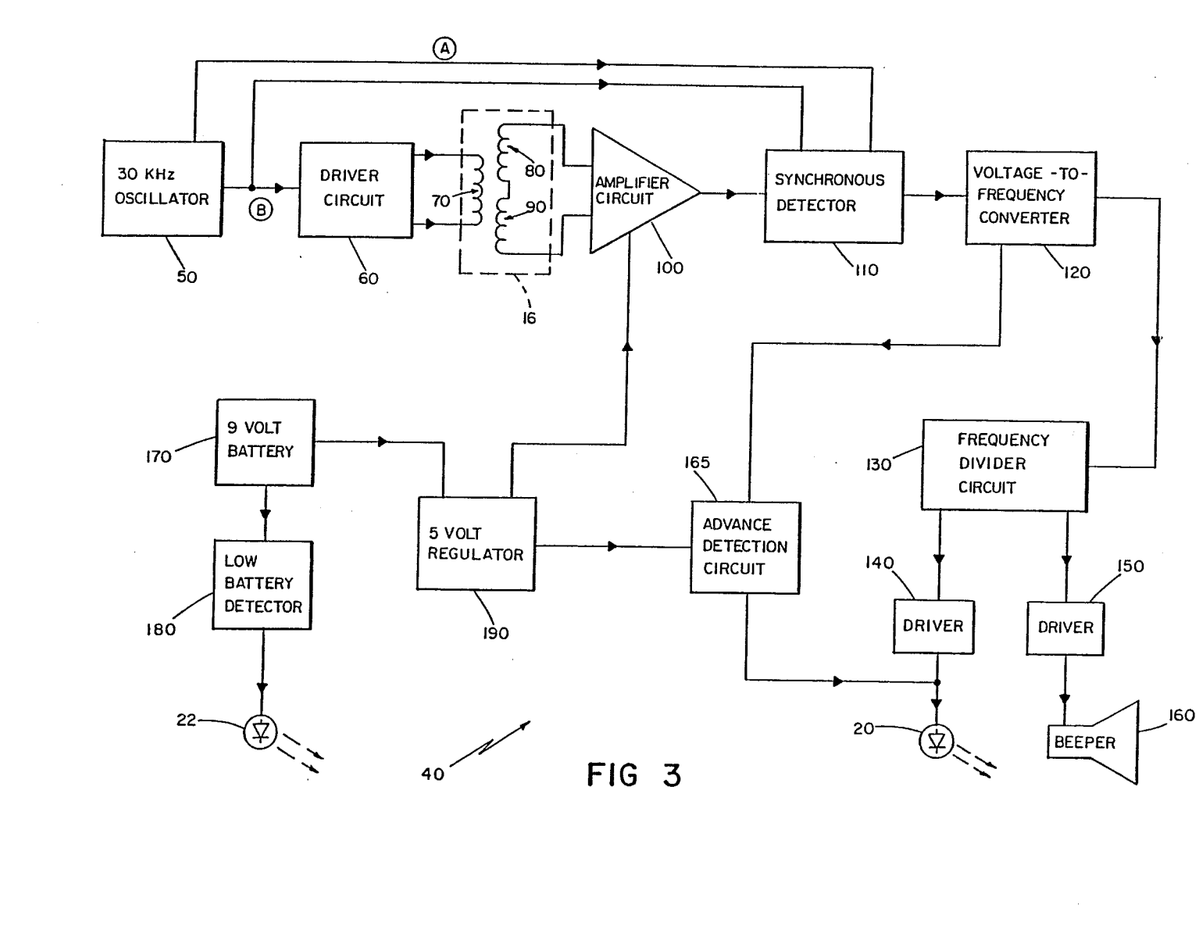
FIG. 3 is a block diagram of the circuit of the invention.
Figure 4:
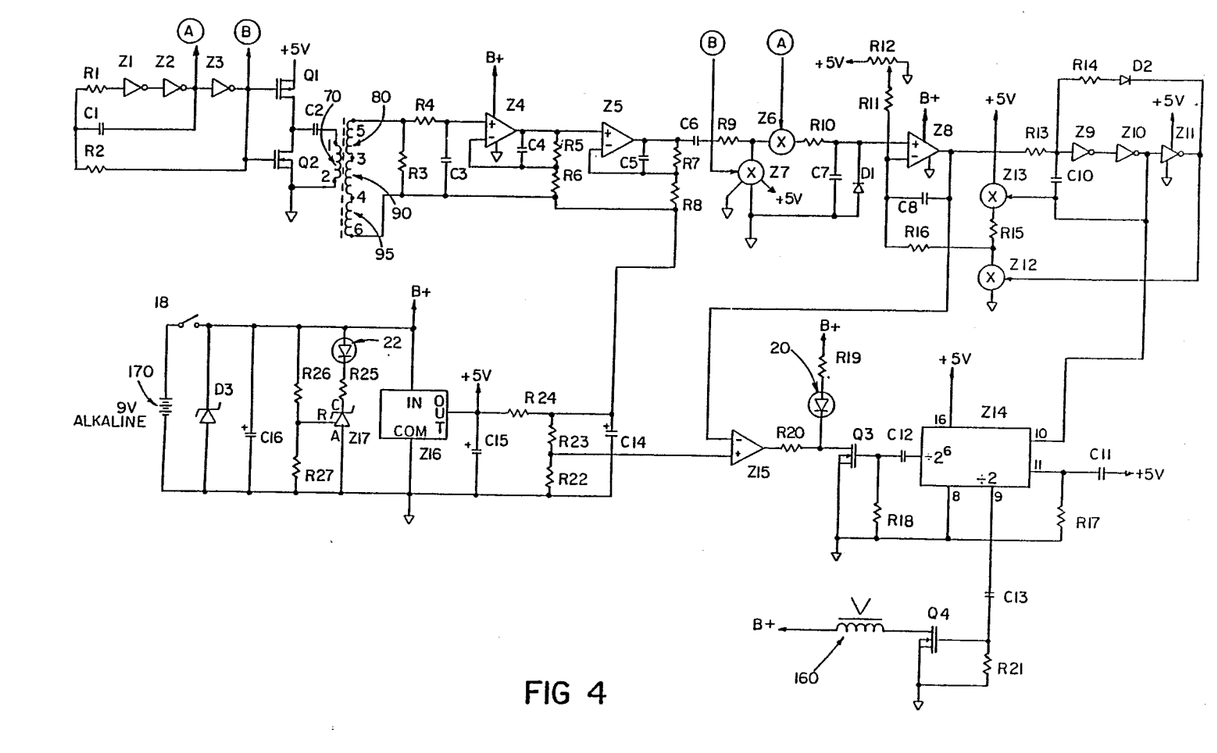
FIG. 4 is a schematic diagram of the overall circuit of the invention.

A block diagram of the circuit 40 of this invention is shown in FIG. 3. The overall circuit 40 basically comprises an oscillator 50 and a driver circuit 60 which activate a primary winding 70 of the probe 14 to produce an electromagnetic field. The probe 14 has a pair of series-connected secondary windings 80, 90 (wired in opposition to each other) the outputs from which are connected to an amplifier circuit 100. The amplifier 100 in turn is connected to a synchronous detector 100, the output of which goes to a voltage-to-frequency converter 120. The frequency output of the converter 120 goes to a frequency divider circuit 130 which feeds a pair of drivers 140, 150 that control the alarm light-emitting diode 20 as well as an audio alarm 160. An advance detection circuit 165, is also provided for the light-emitting diode 20. Also as shown in FIG. 3, a battery 170 for the overall circuit (the connections are represented in FIG. 4) is connected to a low battery detector circuit 180 which controls light-emitting diode 22. The battery 170 also powers a 5 volt regulator 180 which provides specific voltages to several of the circuit elements.

The circuit 40 is specifically shown in FIG. 4. There, the oscillator 50, which is a CMOS gate oscillator, is comprised of three series-connected inverters Z1, Z2 and Z3. A current limiting resistor R1 is connected to the input of the first inverter Z1, and the oscillator circuit is completed by a pair of feedback devices. Specifically, capacitor C1 is connected between resistor R1 and the output of the second inverter Z2, while resistor R2 is connected between resistor R1 and the output of the third inverter Z3. The outputs of inverters Z2, Z3 are complimentary, and they are labeled A and B respectively.

The output B of the last inverter Z3 of the series is connected to the driver circuit 60, which is generally comprised of a pair of complimentary VMOS FETs Q1, Q2. The gates of each FET Q1, Q2 are connected to the output of the oscillator 50. The source of FET Q1 is connected to the =5 volts from the voltage regulator 190, while the source of FET Q2 is connected to ground. The two drains of the respective FETs are connected together and to an d.c. blocking capacitor C2.

The probe 14 is connected to the driver circuit 60. The probe 14 is really a transformer with its primary winding 70 connected between the blocking capacitor C2 of the driver circuit 60 and the source of FET Q2. The two secondary windings 80, 90 are connected in series with a third balancing winding 95 (not shown in the block diagram of FIG. 3.) The specific structure of the transformer is shown in FIGS. 5-8 and will be discussed later. A damping resistor R3 is connected across the secondary windings 80, 90, 95, and the output from the secondary windings is fed through a filter comprising resistor R4 and capacitor C3 to the amplifier circuit 100.

The amplifier circuit 100 comprises two stages. The first stage amplifier Z4 receives any net voltage from the secondary windings 80, 90, and it is connected to feedback capacitor C4 and resistors R5 and R6. The second stage amplifier Z5 is similar. It receives the output from the first stages Z4 and amplifies it further. The second stage amplifier Z5 also has a feedback capacitor C5 and a resistor series R7, R8. A biasing voltage of 3.5 volts is supplied to the two stages Z4, Z5 from the voltage regulator 190.

The output of the two stage amplifier circuit 100 goes to the synchronous detector 110, which is comprised of a pair of analog switches Z6 and Z7. Storage capacitor C6 and resistor R9 are connected in series before the switches Z6, Z7. The switches themselves Z6, Z7 are clocked by the oscillator 50. Specifically, switch Z6 is connected to the output B of the third inverter Z3 of the series of the oscillator 50, while switch Z7 is connected to the complementary output A of the second inverter Z2 of the oscillator 50. To complete the detector 110, capacitor C7 and limiting resistor R10 are connected across the switches Z6, Z7.

The output from the synchronous detector 110 is fed to the voltage-to-frequency converter 120 which is comprised of three stages. The output from the synchronous detector 110 goes to a first input of an error amplifier Z8 for the converter 120, which input is also connected to diode D1. A second input to the error amplifier Z8 is connected through resistor R11 to a variable resistor R12 which sets the threshold for the amplifier Z8 and hence for the device 10. Resistor R12 is designed to be factory adjustable only. The output of the error amplifier Z8 is connected through resistor R13 to a voltage-controlled oscillator, which is comprised of a series of three inverters, Z9, Z10, Z11. The arrangement of the inverters Z9, Z10, Z11 is similar to that for the oscillator 50. Specifically, feedback resistor R14 in series with diode D2 is connected across the three inverters Z9, Z11, Z11, while feedback capacitor C10 is connected between the output of the second inverter Z10 and the input of the first inverter Z9.

The third and final part of the voltage-to-frequency converter 120 is a pair of complementary analog switches Z12, Z13. Switch Z13 is connected to the output of the second inverter Z10, while switch Z12 is connected to the output of the third inverter Z11. The two switches Z12, Z13 are also connected together through resistor R15 and filtered back through resistor R16 to the second input of the error amplifier Z8.

The output of the voltage-to-frequency converter 120, which is actually the output of the second inverter Z10 of its voltage controlled oscillator, is connected to the frequency divider circuit 130 which is primarily a twelve stage binary frequency divider Z14. The output from the voltage-to-frequency converter 120 is connected to the clock of this divider Z14, which has two outputs, a divide-by-two output and a divide-by-sixty-four output. The former is connected to the driver circuit 150 for the 160 beeper. The latter output is connected to the driver circuit 140 for the alarm light-emitting diode 20. The divider Z14, which is actually CMOS Binary Frequency Divider 4040 in the preferred embodiment, has the following connections. Pin 8 is connected to ground, while pin 16 is connected to +5 volts from the voltage regulator 190. Pin 11 is connected to ground through resistor R17 and to +5 volts, also from the regulator 190, through capacitor C11.

The two driver circuits 140, 150 are similar. Specifically, the divide-by-two output from the divider Z14 is connected through capacitor C13 to the gate of a VMOS FET Q4. The drain of FET Q4 is connected to the beeper 160, and its source is connected to ground. Resistor R21 is connected between the source and the gate of FET Q5.

The divide-by-sixty four output of the divider Z14 is connected through capacitor C12 to the gate of VMOS FET Q3. The drain of FET Q3 is connected to the cathode of the alarm light-emitting diode 20. The anode of the diode 20 is connected through resistor R19 to a positive voltage. The source of FET Q3 is connected to ground and also through resistor R18 to its gate.

The advance detection circuit 165 for the light-emitting diode 20 comprises an amplifier Z15, which receives a first input directly from the error amplifier Z8 of the voltage-to-frequency converter 120. The second input for the amplifier Z15 is a 1.5 volt reference voltage from the voltage regulator 190. The output of amplifier Z15 is connected through resistor R20 to the cathode of the light-emitting diode 20.

A nine volt battery 170 is connected through a switch 18 to voltage regulator 190. The regulator 190 is comprised of a three terminal voltage regulator Z16, which receives an input voltage from the battery 170. The output of the regulator Z16 is +5 volts, which it supplies to various circuit components. It is also connected to a voltage divider comprised of resistors R22, R23 and R24 from which other lower reference voltages are supplied to the amplifier circuit 100 (3.5 volts) and the advance detection circuit 165 (1.5 volts). The regulator 190 is completed by bypass capacitor C15 connected across the entire divider, and bypass capacitor C14, which is connected across resistors R22 and R23 of the divider.

The low battery voltage detector 180 is also connected to the battery 170 through switch 18. A programmable shunt regulator Z17 is connected through resistor R25 to the green light-emitting diode 22. The combination is connected across the battery when the switch 18 is closed. Resistors R26 and R27 are also connected across the battery, and the control input of regulator Z17 is connected between them. Capacitor C16 is connected across the resistors R26, R27, while Zener diode D3 is connected across the capacitor C16.

In the preferred embodiment, the following parts are used.

| Resistors | Values | Type* |
|---|---|---|
| R1 | 10K ohms | ±1% |
| R2 | 10K ohms | ±1% |
| R3 | 2.2K ohms | carbon, ⅛ watt |
| R4 | 2.2K ohms | carbon, ⅛ watt |
| R5 | 10K ohms | ±1% |
| R6 | 1K ohms | ±1% |
| R7 | 10K ohms | ±1% |
| R8 | 1K ohms | ±1% |
| R9 | 1K ohms | carbon, ⅛ watt |
| R10 | 1K ohms | carbon, ⅛ watt |
| R11 | 249K ohms | ±1% |
| R12 | 50K ohms | 10 turn potentiometer |
| R13 | 100K ohms | carbon, ¼ watt |
| R14 | 10K ohms | carbon, ¼ watt |
| R15 | 1K ohms | carbon, ¼ watt |
| R16 | 10K ohms | carbon, ¼ watt |
| R17 | 10M ohms | carbon, ¼ watt |
| R18 | 100K ohms | carbon, ¼ watt |
| R19 | 680 ohms | carbon, ¼ watt |
| R20 | 4.7K ohms | carbon, ¼ watt |
| R21 | 10K ohms | carbon, ¼ watt |
| R22 | 15K ohms | carbon, ¼ watt |
| R23 | 20K ohms | carbon, ¼ watt |
| R24 | 15K ohms | carbon, ¼ watt |
| R25 | 680 ohms | carbon, ¼ watt |
| R26 | 15K ohms | ±1% |
| R27 | 10K ohms | ±1% |
| *All resistors are ±5% unless otherwise indicated. | | |

| Capacitors | Value | Type* |
|---|---|---|
| C1 | 1500 pf | 100 v. |
| C2 | 6.8 μf | Tantalum, 20 v. |
| C3 | 510 pf | 100 v. |
| C4 | 100 pf | 100 v. |
| C5 | 100 pf | 100 v. |
| C6 | .1 μf | 50 v. |
| C7 | .1 μf | 50 v. |
| C8 | .01 μf | 50 v. |
| C10 | .001 μf | 50 v. |
| C11 | .1 μf | 50 v. |
| C12 | .1 μf | 50 v. |
| C13 | .022 μf | 50 v. |
| C14 | 6.8 μf | Tantalum, 20 v. |
| C15 | 6.8 μf | Tantalum, 20 v. |
| C16 | 6.8 μf | Tantalum, 20 v. |
| *All capacitors are ceramic unless otherwise indicated. | | |

| Integrated Circuits* | |
|---|---|
| Z1 | CMOS Hex. Inverter 4069/74C04 |
| Z2 | CMOS Hex. Inverter 4069/74C04 |
| Z3 | CMOS Hex. Inverter 4069/74C04 |
| Z4 | Dual Op. Amplifier NE5532. |
| Z5 | Dual Op. Amplifier NE5532. |
| Z6 | CMOS Quad. Analog Switch 4016 |
| Z7 | CMOS Quad. Analog Switch 4016 |
| Z8 | Dual Op. Amplifier LM358AN |
| Z9 | CMOS Hex. Inverter 4069/74C04 |
| Z10 | CMOS Hex. Inverter 4069/74C04 |
| Z11 | CMOS Hex. Inverter 4069/74C04 |
| Z12 | CMOS Quad. Analog Switch 4016 |
| Z13 | CMOS Quad. Analog Switch 4016 |
| Z14 | CMOS Binary Frequency Divider 4040 |
| Z15 | Dual Op. Amplifier LM358AN |
| Z16 | 5V Regulator LM2931A |
| Z17 | Programmable Zener Diode TL431 |
| *It should be noted that many of the integrated circuits can be combined in a single divide, e.g., Z1 Z2, Z3, Z9, Z10, Z11 can all be on a single CMOS Hex. Inverter 4069/74C04. | |

| Transistors | |
|---|---|
| Q1 | VMOS FET VP0104 |
| Q2 | VMOS FET VN0106 |
| Q3 | VMOS FET VN0106 |
| Q4 | VMOS FET VN0106 |

| Diodes | |
|---|---|
| D1 | 1N 4148 (small signal) |
| D2 | 1N 4148 (small signal) |
| D3 | 1N4744, Zener Diode (15 v. 1 watt) |
| Light Emitting Diode 20 | Red HLMP-3301 |
| Light Emitting Diode 22 | Green HLMP-3507 |

| Miscellaneous | |
|---|---|
| Beeper 160 | Panasonic 14R06C |
| Switch 18 | Push-button C + K 8121-A-5 |

Figure 5:
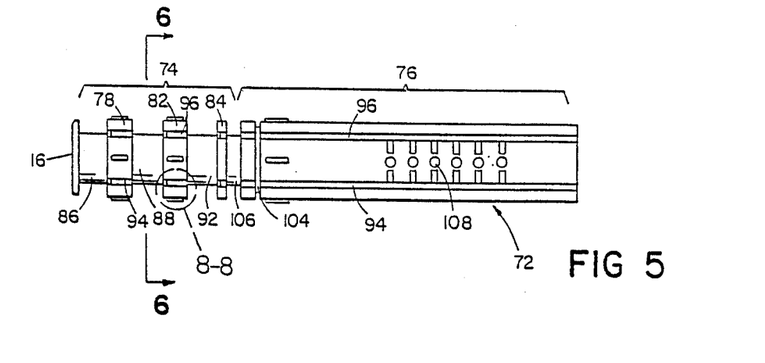
FIG. 5 is a top view of the core of the probe of the invention.
Figure 6:
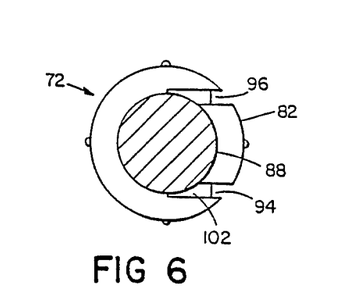
FIG. 6 is a cross-sectional view of the core of the probe of FIG. 5 taken along lines 6—6.
Figure 7:
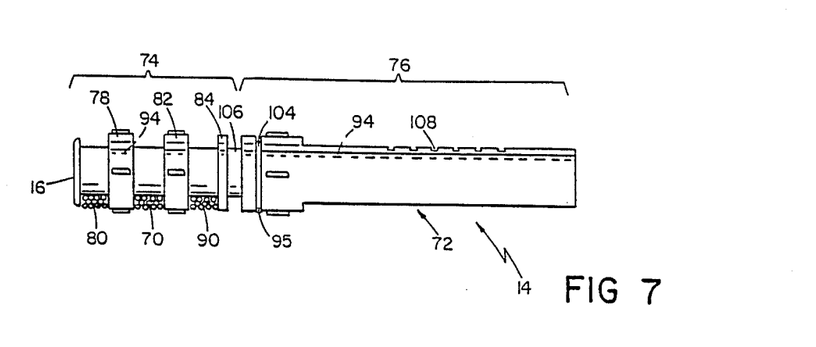
FIG. 7 is a cross-sectional view of the probe with the windings in places.

The probe 14 is shown in detail in FIGS. 5-8. As best shown in FIGS. 5 and 7, the probe 14 comprises a generally cylindrical core 72. The core 72, which is plastic (polycarbonate with a 10% glass fill in the preferred embodiment), is comprised of an extended portion 74, which houses the windings 70, 80, 90 and extends beyond the detector 10 itself, as shown in FIG. 1. It also comprises a mounting section 76, which is disposed inside the detector 10 and used to connect the windings to the circuit 40.

The extended portion 74 of the probe 14 comprises the detection tip 16 followed by a pair of thick walls 78, 82 and a thin expansion wall 84. Slots 86, 88 and 90 are formed between the walls 16, 78, 82, 84. The slots are machined into the core 72. As shown in FIG. 7, the primary winding 70 is disposed in the slot 88 formed between the two thick walls 78, 82. Secondary winding 80, which will be nearest the patient when the device 10 is in use, is disposed between the detection tip 16 and the first of the thick walls 78. Secondary winding 90 is disposed between the second thick wall 82 and the expansion wall 84. The distance from the mid-point of the primary winding 70 to the detection tip 16 and to the expansion wall 84 is the same. Thus, the two secondary windings 80, 90 are symmetrically disposed with respect to the primary winding 70. (Only a few layers of each winding is shown in FIG. 7.)

The mechanical stability of the windings is important because any changes in the flux caused by the presence of the metal band 32 on the endotracheal tube 24 will be small to begin with. Thus, very little instability may produce a signal that would correspond to an actual detection one. To make the windings as stable as possible, all the windings 70, 80, 90 are wound as tightly and as evenly as possible. This can be done by specialized transformer companies such as the Newton Engineering Company of Newton, Mass.

As shown in FIGS. 5, 6, there are a pair of horizontal grooves 94, 96 to carry the lead wires for the windings into the slots 86, 88, 92 where the windings will be wound. Groove 94 carries the wires 98 (shown in FIG. 8) for the primary winding 70, while groove 96 carries the lead wires (not shown) for both secondary windings 80, 90. The lead wires for each winding are twisted in pairs with not less than ten twists per inch.

Figure 8:
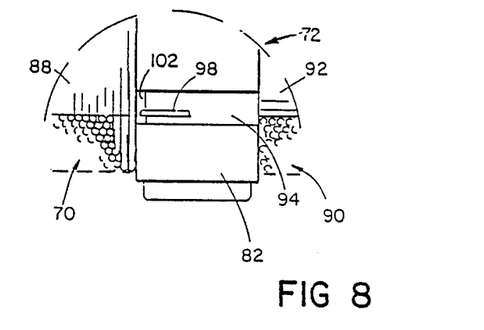
FIG. 8 is an enlarged view of the circled portion of the core of the probe of FIG. 5 with the winding wire in place.

As shown in FIG. 8, the lead wires 98 for the primary winding 70 are fed down a vertical groove 102 in the face of the second thick wall 82. This permits the winding 70 to be made on the core 72 in even layers. Similar slots are provided for the secondary windings 80, 90. Before the winding is actually made, however, the surface of the slot (86, 88, 92) on which the winding is to be made is coated with an epoxy that has a coefficient of thermal expansion approximately equal to the core material itself. ISOCHEM No. 213 resin with 67LK hardener is used in the preferred embodiment, and it limits mechanical movement of the windings.

Each winding is then made on the core 72, and in the preferred embodiment, each winding has 300 turns of #38AWG wire. After all the layers are complete, the entire winding is vacuum impregnated with the same epoxy. Alternately, epoxy may be brushed on after each layer is complete. In either case, this provides mechanical and thermal stability.

Once the initial windings 70, 80, 90 are complete, the secondary windings 80, 90 are checked for balance. Ideally, each secondary winding should have the same number of turns. However, if for any reason the two secondary windings 60, 70 are not precisely balanced, this can be corrected by the fourth winding 95, which has a few turns and which is placed in slot 104, shown in FIGS. 5 and 7. The epoxy treatment for the fourth winding 95 is the same as for the others.

The lead wires from the windings are fed in their respective horizontal grooves 94, 96 back to the mounting portion 76 of the core 72. The mounting portion 76 has a series of six holes 106, shown in FIGS. 5, 7, into which connector pins (not shown) are attached. The lead wires are connected to the pins which lead to the remainder of the circuit 40. Specifically, the lead wires from the primary are connected to the first two pins. The secondary winding 80 nearest the tip 16 is connected to the third and fifth pin, while the other secondary winding 90 is connected to the third and fourth pins (thereby connecting the secondary windings in series). The fourth winding 95 is connected to the sixth pin and the fourth pin. The direction of this winding 95 depends upon which of the secondary windings 80, 90 needs the additional windings.

The coefficient of thermal expansion is important in the probe 14. The core 72 should not have a coefficient of thermal expansion greater than $1.8 \times 10^{-5}$ inches per ° F. and the epoxy used to bind the windings should have a similar one. The aforementioned core material and epoxy are suitable. Furthermore, a special expansion slot 106 is disposed adjacent to the expansion wall 84 for the secondary winding 90 farthest from the tip 16. This means that any thermal expansion of the secondary windings 80, 90 will be more symmetrically balanced.

Once assembled, the probe 40 is further stabilized by cycling it between high and low temperatures. It is first baked at 60° C. for 24 hours. Then, it is cycled between −15° C. and 70° C. ten times. This accelerates the stabilization process and the bonding of the wire to the core 72. The resulting probe is highly stable, both mechanically and thermally.

Operation

Figure 2:
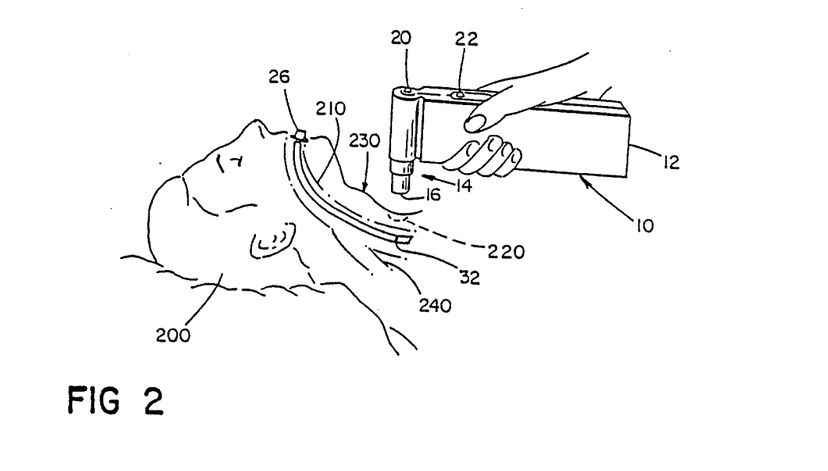
FIG. 2 is a perspective view of the invention in use.

With reference to FIG. 2, the detector 10 operates as follows. The tube 24 is placed in a patient 200 with the connector 26 disposed outside the patient's mouth. The tube 28 extends into the trachea 210 with its distal end 30 disposed beneath the suprasternal notch 220, which is the proper position for it. The detector 10 is turned on by the switch 18, and if the battery has sufficient power, the green light-emitting diode 22 on the top of the instrument will come on. The operator then takes the detector 10 and directs the detecting tip 16 of the probe 14 over the front 230 of the patient's throat. When the tip 16 is positioned directly over the metal band 32, the beeper 160 will sound and the red light-emitting diode 20 will go on and blink rapidly. Just before the band is located, the diode 20 will turn on and blink slowly to indicate that detection is imminent. If, however, the tube 24 has entered the esophagus 240, the detector 10 will not detect the band 32 because it will be too far away to disturb the field. This requires that the amount of metal in the band be limited It should be limited to between 0.00543 and 0.00977 grams for an adult tube, and between 0.00274 and 0.00585 grams for a pediatric tube. (The distance to the esoPhagus is shorter in a child or infant.)

Specifically, the circuit 40 of this invention operates as follows to detect the band 32. The three series-connected inverters Z1, Z2, Z3 of the oscillator 50 produce an output signal, the frequency of which depends upon resistor R2 and capacitor C2. The reason is that resistor R2 provides negative feedback to return the input of the inverter series to its threshold, while capacitor C2 provides positive feedback, limited by resistor R1, to drive that input above the threshold. As a result of the values chosen for these parts in the preferred embodiment, the output frequency of the oscillator 50 is 30 KHz, and the waveform is approximately square. The primary output, signal B, is sent to the driver circuit 60 to excite the primary winding 70.

The driver 60 improves the operating efficiency of the detector 10. FETs Q1, Q2 (which conduct between their drains and sources when turned on) buffer the output of the oscillator 50, and the arrangement is such the energy needed to excite the primary winding 70 is recycled through the "on" FET to the filter capacitor. Thus, the power is not simply dissipated by the primary winding 70.

The relatively large a.c. current sent through the primary winding 70 from the driver circuit 60 creates a magnetic field which encompasses the two secondary windings 80, 90 and any fourth balancing winding 95 that exists. This induces voltages in each of the secondary windings 80, 90, which cancel each other out when the field is balanced (the same but opposite voltages being induced in each secondary winding). Thus, when the field is balanced, the net output from the probe 14 is zero and will remain such despite temperature and other similar changes.

The output from the probe 14 becomes a net voltage when the field becomes unbalanced. If a piece of ferromagnetic material such as that of the metal band 32 is near the tip 16 of the probe 14, it will draw more magnetic flux through the nearest secondary winding 80. This causes an increase in the a.c. voltage produced by that winding 80, and as there is no corresponding increase in the voltage from the other secondary winding 90, this results in a net output voltage for the probe 14. The output voltage increases exponentially as the metal approaches the secondary winding 80 along its axis. However, the range of the field is deliberately limited, and the net output voltages are routinely quite small. As a result, the signal needs to be amplified before actually "detecting" it.

As a result, any output from the secondary windings 80, 90 is sent to the amplifier circuit 100, after resistor R3 eliminates any ringing and after resistor R4 and capacitor C3, which operate as a low pass filter, screen out any radio frequency interference. After that, the signal goes to the first stage amplifier Z4 of the amplifier circuit 100. The amplified signal from the first stage amplifier Z4 is then amplified again by the second stage amplifier Z5. Each provides a noninverted gain of 11 so that the overall gain for the amplifier circuit 100 is about 120. The reason two amplifiers having gains of 11 are used instead of one having a gain of 120 is that it is less demanding of amplifier gain-bandwidth to have the dual stage amplification. Moreover, the selection of the amplifiers is important for another reason. A high gain-bandwidth is required to guarantee gain stability at the frequency of the signal from the secondary windings 80, 90 despite temperature changes. This is the reason an NE5532 amplifier with a 10 MHz bandwidth and fast slew rate is used in the preferred embodiment. It exhibits no impact on signal amplitude with temperature change.

An operating voltage of 3.5 volts for the two amplifiers Z4, Z5 is provided by the voltage regulator 190 (specifically from the voltage divider formed by resistors R22, R23, R24), and capacitors C4 and C5 respectively limit the two stages to about 160 KHz to limit noise pickup and to prevent any oscillation due to stray capacitance at the inverting inputs of the amplifiers. The amplified output from the amplifier circuit 100, which is indicative not only of the presence of the metal band 22 in the field but also (by the signal magnitude) its proximity to the tip 16, is then sent to the synchronous detector 110.

The synchronous detector 110 is clocked by the 30 KHz oscillator 50, and as a result, it converts to d.c. only those components of the a.c. input signal which are odd harmonics of the clock from the oscillator 50. This results in excellent rejection of signals not originating from the secondary windings 80, 90, and the a.c. to d.c. conversion is also very accurate due to the absence of any forward biased diode voltage drop. As a result, the converter 110 has excellent temperature stability, Specifically, the output from the secondary windings 80, 90 and from the amplifier circuit 100 is in phase with the output signal B from the third inverter Z3 of the oscillator 50. It is also 180° out of phase with the output signal A from the second inverter Z2 of the oscillator 50. When the output from the amplifier circuit 100 goes low, analog switch Z7 is turned on by signal A. This causes the low output voltage from the amplifier circuit 100 to be stored by capacitor C6. Resistor R9 controls the time constant for charging capacitor C6, which serves to reject transients. When the output voltage from the amplifier circuit 100 goes high, the other analog switch Z6 is turned on by signal B, and the difference between the high and low output voltages from the amplifier circuit 100 is stored across capacitor C7. Resistor R10 limits the amount of charge which can be lost by capacitor C7 if both analog switches Z6, Z7 simultaneously conduct for a short period as they change states. The resulting d.c. output is sent to the voltage-to-frequency converter 120.

The three series-connected inverters Z9, Z10, Z11 of the converter circuit 120 operate in much the same manner as the oscillator 50. In particular, the oscillator formed by these inverters Z9, Z10, Z11 is active when there is an output from the error amplifier Z8. In order for that to occur, the d.c. output signal from the synchronous detector 110 must be above a certain threshold level set by variable resistor R12. The setting of resistor R12 depends upon the sensitivity desired for the detector, and resistor R12 is set at about 2.5 volts in the preferred embodiment. A lower setting would make the detector 10 more likely to detect the metal band 32 if the distal end 30 of the tube 24 is in the esophagus 240.

When active (when the input voltage from the synchronous detector 110 exceeds the threshold voltage), the current from the error amplifier Z8 through resistor R13 charges capacitor C10. This raises the voltage at the input to the first inverter Z9. Capacitor C10 also provides positive feedback from the output of the second inverter Z10 to help drive the inverter input through its threshold. As a result, the output of the inverter Z9 switches low, as does the output of the third inverter Z11. The low voltage at the output of the last inverter Z11 coupled with the high voltage at the input of the first inverter Z9 forward biases diode D2, which along with resistor R14 is shunted between them. This permits a rapid discharge of capacitor C10. When it discharges, the inverters change state. The cycle then repeats with capacitor C10 charging and discharging. The speed at which this happens (and thus the frequency of the oscillator) depends upon the speed at which the capacitor C10 charges. The net result is two complementary pulse train on the outputs of the second inverter Z10 and the third inverter Z11, with the same amplitude, but with the pulse width set by capacitor C10 and resistor R14 and the repetition rate set primarily by the output voltage from the error amplifier Z8. As a result, the output from inverter Z10, is a pulse train the frequency of which depends on the magnitude of the net voltage from the secondary windings 80, 90.

To stabilize the voltage-to-frequency circuit 120, the pulse trains from the inverters Z10, Z11 are converted back to voltages and fed into the error amplifier Z8 as part of a servo/loop. Specifically, the pulse train from inverter Z10 goes to analog switch Z13, while the pulse train from inverter Z11 goes to analog switch Z12. As the pulse trains are complementary, a pulse from inverter Z10 causes the analog switch Z13 to turn on (while analog switch Z12 is turned off). This results in a pulse train at the output of switch Z13, the average voltage value of which increases as the frequency of the pulses increases. The pulse train is filtered by resistor R16 and capacitor C8 and is sent as a feedback signal to the second input of error amplifier Z8.

The error amplifier Z8 continuously compares the input voltage from the synchronous detector 110 with this feedback signal from the oscillator and then controls its output voltage to the oscillator so that the inputs remain equal. This, however, assumes that the input from the detector 110 is above the threshold voltage set by resistor R12. When the input voltage is below that level, there is no output to the oscillator, and the oscillator is inactive.

When the oscillator is operating, the pulse train from inverter Z10 is sent to the frequency divider circuit 130. It is received by the clock of the twelve stage binary frequency divider Z14. The divide-by-two output from the divider Z14 is sent to driver 150 for the beeper 160. Capacitor C13 and resistor R21 differentiate the signal into pulses which go to the gate of FET Q4 which drives the beeper 160. The beeper 160 sounds when the secondary windings 80, 90 produce a net voltage above the set threshold level for the voltage to frequency circuit 120. The loudness depends upon the values of resistor R21 and capacitor C13.

The frequency divider 130 also supplies an output through its divide-by-sixty-four output to the driver 140 for the red light-emitting diode 20. As with the driver 150 for the beeper 160, capacitor C12 and resistor R18 of the driver 120 differentiate the output to pulses which are used to turn on FET Q3 thereby controlling the blinking rate of the light-emitting diode 20. The on-time for the diode 20 is set by the capacitor C12 and resistor R18, and it blinks more rapidly as the probe 14 comes closer to the metal band 32.

The light-emitting diode 20 also illuminates dimly when the metal band 32 is just coming into range because of the advance detection circuit 165. This is useful to alert the operator to the possible detection of the band because the field is a very narrow one, and a relatively small lateral movement of the detector 10 will take the band 32 out of range. The output of the error amplifier Z8 is fed to the comparison amplifier Z15 which also receives a 1.5 volt reference from the voltage divider R22, R23, R24 of the voltage regulator 190. Essentially, the amplifier Z15 compares the two signals. If the output of error amplifier Z8 has risen out of saturation (about 2.5 volts), the output of amplifier Z15 will go low, and the light-emitting diode 20 will light dimly indicating the converter 120 has just begun to produce a frequency or is about to do so.

The voltage regulator circuit 190 generally provides +5 volts to the critical circuitry. The regulator Z16 will do so even if the battery level drops to as low as 5.5 volts from its 9 volt level. The voltage divider R22, R23, R24 merely divides the output voltage so that several lower reference voltages can be supplied to portions of the circuit. Specifically, 3.5 volts is provided to the amplifier circuit 100 to set the operating point for amplifier stages Z4, Z5. Also, 1.5 volts is provided for amplifier Z15 in connection with activating the light emitting diode 20 when the metal band 32 begins to come into range.

Finally, the low battery voltage detector 180 uses resistors R26, R27 to provide a divided measure of the battery voltage for the control input of shunt regulator Z17. When the battery voltage is greater than about 6.25 volts, the threshold of the regulator Z6 is exceeded, and it conducts. The green light-emitting diode 22 lights as a result. When the battery level falls below 6.25 volts, the regulator Z17 ceases conduction, and the diode 22 does not come on.

Other embodiments will occur to those skilled in the art.

What we claim is:

1. A device for accurately detecting at a specific limited distance the position of an object having ferromagnetic properties inside biological tissue, while being relatively insensitive to changes in external temperature and the like, comprising:

a probe having a primary winding and at least two secondary windings, a means for producing an alternating output to activate said primary winding, said primary winding, when activated, generating a limited field which induces a.c. voltages in said secondary windings, said voltages in said secondary windings being approximately equal and cancelling each other so that said probe has an approximately zero output voltage when the object to be detected is outside a specific limited distance from one of said secondary windings, but creating unequal voltages in said secondary windings which do not cancel each other so that said probe has a net alternating voltage when the object is within a specific limited distance from one of said secondary windings, a detection means connected to said secondary windings for detecting any net alternating voltage from said probe, said detection means comprising a means for amplifying any such net alternating voltage from said probe, and a means for converting any such net alternating voltage as amplified by said means for amplifying to a d.c. voltage, the magnitude of which reflects the proximity of the object to one of said secondary windings, a conversion means for converting the d.c. voltage from said means for converting, said conversion means comprising a voltage to frequency converter having a threshold voltage means which sets a level that must be exceeded by the d.c. voltage from said means for converting in order to produce an output signal from said conversion means thereby limiting the detection distance and providing insensitivity to external temperature, said voltage to frequency converter including an error amplifier connected to an oscillator circuit having a pair of outputs, said outputs of said oscillator circuit being complementary and respectively connected to a pair of analog switches which form a servo loop with an input of said error amplifier so that said error amplifier compares each output of said oscillator circuit with the input received by said error amplifier from said means for converting, one of said oscillator circuit outputs providing the output signal from said conversion means, said means for converting further comprising a synchronous converter, said synchronous converter having first and second analog switches, each said switch being alternately triggered by a different, complementary output from said means for producing, said synchronous converter also having a first capacitor, said first capacitor being charged with the low voltage from any amplified net alternating output from said means for amplifying when said first analog switch is activated by a first output from said means for producing, an alarm means which is activated by the output signal from said conversion means and a power source, said power source connected to said means for producing, said detection means and said conversion means.

2. The device of claim 1 wherein said probe has three secondary windings, two of said secondary windings comprising main secondary windings for generating the net alternating voltage for said probe if the object is within a specific limited distance, while the third of said secondary windings comprises a small, balancing winding connected in series with one of the other secondary windings to help balance the voltage induced in them when the object is not within a specific limited distance.

3. The device of claim 1 wherein said secondary windings are connected series.

4. The device of claim 1 wherein said means for producing comprises an oscillator which drives a driver circuit connected to said primary winding.

5. The device of claim 4 wherein said driving oscillator is a 30 KHz oscillator comprising a series of three inventers.

6. The device of claim 4 wherein said driver circuit comprises a pair of FETs which receives the output of said oscillator and provides a high alternating current to said primary winding.

7. The device of claim 6 wherein said primary winding is disposed between a blocking capacitor connected between said FETs and one of said FETs so as to return current through whichever FET is conducting to a filter capacitor for said means for producing to improve efficiency.

8. The device of claim 1 wherein said means for amplifying comprises a pair of noninverting amplifiers in series, said series amplifiers each producing a gain in any net alternating voltage for said secondary windings.

9. The device of claim 8 wherein said overall gain for said pair of amplifiers is approximately 120.

10. The device of claim 1 wherein said synchronous converter has a second capacitor which charges with the difference between the high and low voltage from any amplified net alternating output from said means for amplifying, when said second analog switch is activated by a second output from said means for producing, which second output is in phase with that used to activate said primary winding and 180° out of phase with said first output used to activate said first analog switch.

11. The device of claim 1 wherein said error amplifier has a threshold voltage which must be exceeded by said d.c. voltage from said means for converting in order to produce an output from said error amplifier.

12. The device of claim 11 wherein each said output of said oscillator circuit is a pulse signal having a frequency which is proportional to the magnitude of the voltage output of said error amplifier.

13. The device of claim 12 wherein the pulse signal from said oscillator circuit is the output signal used to activate said alarm means.

14. The device of claim 12 wherein the frequency of said oscillator circuit is controlled by charging and discharging a second capacitor, the rate of charging and discharging of which depends upon the magnitude of the voltage from said error amplifier.

15. The device of claim 14 wherein said oscillator circuit includes a resistor and diode in series connected across three series connected inverters which produce the signal output from said conversion means, said resistor and diode serving to discharge said second capacitor when the input of the first of said three inverters goes high as a result of said second capacitor being charged, the discharge causing said inverters to change states.

16. The device of claim 1 wherein said alarm means comprises a frequency divider circuit which divides the output signal from said conversion means and sends the divided signals to a light-emitting diode and an audio alarm beeper.

17. The device of claim 16 wherein said alarm means includes first and second driver circuits, associated respectively with said diode and said beeper, each said driver circuits being comprised of an FET which provides a pulsed output to activate said diode and said beeper.

18. The device of claim 1 further comprising an advance detection circuit, said advance detection circuit receiving a secondary output from said conversion means which secondary output indicates that said conversion means is about to produce a signal output for said alarm means, and based on a comparison of the secondary output with a reference voltage, said advance detection circuit activates said alarm means so as to give advance warning of an actual signal output from said conversion means.

19. The device of claim 1 further comprising a voltage regulator which is connected to said power source and which provides through a voltage divider various reference voltages for the elements of said device.

20. The device of claim 19 wherein said voltage divider comprises a series of resistors.

21. The device of claim 1 further comprising a low voltage battery detector comprising a programmable zener diode which activates a light-emitting diode whenever said power source is producing at least a certain minimum voltage.

* * * * *